United States Patent [19]

Rau

[11] Patent Number: 4,685,466
[45] Date of Patent: Aug. 11, 1987

[54] MEASURING SENSOR FOR THE NON-INVASIVE DETECTION OF ELECTRO-PHYSIOLOGICAL QUANTITIES

[76] Inventor: Günter Rau, Mauerkircherstrasse 45, 8000 München, Fed. Rep. of Germany, 80

[21] Appl. No.: 823,351

[22] Filed: Jan. 28, 1986

[30] Foreign Application Priority Data

Jan. 29, 1985 [DE] Fed. Rep. of Germany ....... 3502913

[51] Int. Cl.⁴ ............................................... A61B 5/04
[52] U.S. Cl. ................................... 128/639; 128/640; 128/642; 128/643
[58] Field of Search ............................... 128/639–644, 128/710

[56] References Cited

U.S. PATENT DOCUMENTS

| | | | |
|---|---|---|---|
| 3,505,993 | 4/1970 | Lewes et al. | 128/643 |
| 3,545,432 | 12/1970 | Berman | 128/640 |
| 3,572,323 | 3/1971 | Yuan | 128/640 |
| 3,623,477 | 11/1971 | Trent | 128/644 |
| 3,776,228 | 12/1973 | Semler | 128/710 |
| 3,826,244 | 7/1974 | Salcman et al. | 128/642 |
| 4,004,578 | 1/1977 | Palmius | 128/642 |
| 4,350,164 | 9/1982 | Allain, Jr. | 128/639 |

FOREIGN PATENT DOCUMENTS

| | | | |
|---|---|---|---|
| 2064781 | 7/1972 | Fed. Rep. of Germany | 128/643 |
| 2152808 | 4/1973 | Fed. Rep. of Germany | 128/643 |
| 2552035 | 5/1977 | Fed. Rep. of Germany . | |
| 2555281 | 6/1977 | Fed. Rep. of Germany . | |
| 3025955 | 1/1982 | Fed. Rep. of Germany . | |
| 2088780 | 1/1972 | France . | |

*Primary Examiner*—Lee. S. Cohen
*Attorney, Agent, or Firm*—Parkhurst & Oliff

[57] ABSTRACT

The measuring sensor for biomedical signals, above all electro-physiological quantities, in contrast to invasive needle and wire electrodes introduced into the body through the physiological "skin" barrier, and in contrast to pure surface electrodes merely brought in contact with the body surface, has as its essential part one or more short needle points which penetrate into the uppermost largely cast-off cell layers of the horny skin and which are retained by means of a preferably flexible mounting. The technique which can be carried out by means of the measuring sensor can be called quasi-invasive, although the needle point does not pass through the skin. The measuring sensor is suitable for detecting and measuring the electrophysiological quantities and for electrical stimulation.

8 Claims, 12 Drawing Figures

MEASURING SENSOR FOR THE NON-INVASIVE DETECTION OF ELECTRO-PHYSIOLOGICAL QUANTITIES

BACKGROUND OF THE INVENTION

The invention relates to a measuring sensor for noninvasive detection of electro-physiological quantities.

In medical and physiological measurements, electrodes are used to detect a multiplicity of electrical signals (for example electrocardiogram, electromyogram, electroneurogram, electroencephelogram, etc.) for purposes of diagnosis and therapy. Thus, for example, French Patent Specification No. 2,088,780 describes an EEG electrtode with a plurality of individual needle-like pins which are fastened to a common baseplate at a short distance from one another and which, during measurement, do not penetrate into the skin, but improve skin contact and transition resistance by means of a locally higher surface pressure. A further example of electrodes of this type, to which reference may be made, is the conducting electrode described in German Offenlegungsschrift No. 3,025,955 for detecting bioelectrical activity of hairy parts of the body. Such reference discloses a plurality of conducting pins mounted in an electrode housing so as to be displaceable counter to compression and contact springs which ensure sufficient contact pressure against the skin surface. The signals to be derived are generated inside the body which can be conceived as a volume conductor with an ionconducting medium of moderate specific conductivity. In electrical terms, the skin represents an enveloping surface of the volume conductor and has at the same time a very high complex specific resistance. The electrical and mechanical properties of the skin therefore play a special part, since it can influence the measurement result greatly (see G. Rau "The Influence of Electrode and Skin Impedance in Measurements with Surface Electrodes (EMG)", Biomedizinische Technik 18, 23 to 27 (1973)).

The use of invasive electrodes which are pricked through the skin into the body, for example in the form of wire or needle electrodes, largely eliminates the influences of the properties of the skin on the measurement. However, other disadvantages have to be taken into account at the same time. The examinations are painful, which also presents serious problems especially when children are examined, and are scarcely tolerable when the measurements are repeated. There is also an increased potential danger of infection, since the skin, as a physiological barrier, is penetrated completely. Consequently, possibilities of non-invasive measurement are sought, and if at all possible, surface electrodes are preferred.

However, the use of surface electrodes again presents a series of problems indicated below merely by key phrases:

(1) The transfer from the electrode material to the electrolyte;

(2) The electrical and mechanical coupling of the skin;

(3) The electrical and mechanical properties of the skin itself.

The skin has a very high complex electrical resistance, for example impedance values of several $M\Omega/cm^2$ can be observed with measuring currents of a frequency of 1 Hz. This resistance is also highly nonhomogeneous over the extent of the skin surface. Most of the electrical impedance is centered in the horny layer, that is to say in the stratum corneum conjunctum, namely up to approximately the tenth to fourteenth cell layer from outside. The outermost cell layers are in the process of dying and being cast off (see P. Schulz, "New Methods and Investigations of the Electrical Resistance of Human Skin Under Direct and Alternating Currents", thesis Freiburg 1966).

Also, when pressure is exerted on the skin surface, (a) a variation or modulation of the skin resistance occurs, and (b) a voltage is generated on the skin between the inside and ouside (skin potential). In any measurement, these effects produce interfering signals which are called "movement artefacts". These also include the disturbances caused by relative movements of the electrode surface and the skin surface; these are reduced by means of different methods of fastening the electrodes, such as adhesion, clamping with rubber bands, suction and the like. A customary method by which an attempt is made to eliminate the skin influences by scraping off or cutting off the uppermost skin layers often causes considerable injury together with a danger of infection.

Another possibility of reducing the influence of movement artefacts on the measurement, but without having to scrape off or cut off the upper cell layers of the skin, is mentioned in German Offenlegungsschrift No. 2,555,281 which is the starting point for the invention. It is known from this publication to fashion points on measuring-sensor electrodes, so that they penetrate such a little way into the skin surface that only the uppermost horny cell layers are pierced. However, these are large-area electrodes having a plurality of points which each form a unit in elctrical terms.

SUMMARY OF THE INVENTION

In contrast to this state of the art, the object on which the invention is based, while ensuring a reduced influence of the electrical property of the skin on the measurement, is also to make it possible to detect electro-physiological quantities locally.

In a measuring sensor according to the invention, the electrode resembling a needle point penetrates into the uppermost horny cell layers of the skin and thus passes through the resistance barrier (approximately 10 to 15 cell layers from the skin surface). An exceptionally effective fastening of the electrode is also obtained as a result, so that all movement artefacts are greatly reduced.

Since the point only penetrates into those cell layers which are in any case in the process of being cast off, neither blood nor body fluid comes in contact with the point of the electrode or escapes from the skin after the point has been removed. There is, therefore, scarcely any danger of infection, so that in terms of this advantage it bears comparison with pure surface electrodes. The "indentation points" in the skin which are produced by the electrode points disappear after approximately 30 minutes at the latest. No sensation of pain can be observed, since the skin receptors are all located in deeper layers of the skin.

By means of the invention, surface electrodes of minimum area have been produced, and these are suitable for local conduction and therefore, in comparison with all previous methods and surface electrodes, make it possible to obtain more effectively reliable and authentic measurement results with considerably reduced interfering signals (movement artefacts, noise, etc.).

There is no need to use electrode paste or electrode jelly which are usually required on conventional surface electrodes. When they are used as stimulation electrodes, the reduced skin resistance again has a very positive effect, since relatively high stimulating currents (stimulating-current densities) can be obtained even when the voltage values are relatively low. The unpleasant or painful sensations experienced during stimulation are reduced, and the stimulating effect can be obtained very locally. Furthermore, by means of a special electrode arrangement, potential fields can be detected very effectively in both time and space, so that, for example, reaction times can be measured with very high accuracy from the surface.

By means of the measuring sensor according to the invention, a substantial improvement is achieved where measurements with surface electrodes of minimum area are concerned, particularly since the electrical and mechanical properties are improved because of the way in which the electrode is applied. The point of the electrode penetrates only a little way into the uppermost layers of the skin, and the depth of penetration can be influenced by the length of the point and the point angle. The mounting for the needle points can be formed from rigid plastic or from flexible plastic or rubber, depending on the particular use.

Metals or metal alloys (for example, steel, silver, platinum, copper, brass, etc.), electrically conductive plastic or semiconductor material (for example, even carbon electrodes) serve as electrode material. The surface can be covered with suitable material, for example with metal, and its surface can be coated in turn with a salt. One possibility here is, for example, a steel point with a silver coating and a deposit of AgCl. These measures improve the properties of the transfer from the electrode to the electrolyte. In special cases, it may be necessary to cover the point with an insulating protective layer (for example, enamel) and remove the insulation only at the very tip of the end of the point.

Because of the weak signals which can be conducted very locally by means of this electrode, there is a possibility of achieving a substantial improvement by attaching directly to the electrode a micro-miniaturized semiconductor arrangement for active impedance matching and/or amplification. Interference which is introduced into the useful signal via leads and their electrical properties (in particular capacitances, etc.) is greatly reduced as a result. Various screening measures can be taken in or around the electrode, for example by means of netting or foil conductor materials which extend parallel to the skin surface so as to cover the electrodes.

For specific measuring functions, a further improvement can be achieved if the invention is extended to cover several needle points which are arranged close to one another and which, being connected electrically in parallel, act as a common electrode. This allows for the fact that the electrical resistance of the skin is not homogeneous over its surface. Because multiple points are used, it is highly probable that one of the points encounters a skin zone of low resistance, so that the resistance is only slight whenever it is applied. Since the mechanical deformability of the skin is limited, for example three or four points arranged at a distance of approximately 0.5 mm from one another press into the skin less than a single point. The length of the multiple points can therefore be increased somewhat.

BRIEF DESCRIPTION OF THE DRAWINGS

The invention and advantageous details are explained in more detail below in exemplary embodiments with reference to the drawings, in which.

DETAILED DESCRIPTION OF THE PREFERRED EMBODIMENTS

FIG. 1 shows a measuring sensor with a single electrode. The different embodiments differ from one another in the varying design of the mounting 2, in which a needle point 1 is embedded. The electrical connection, for example soldered on, is designated by 3.

Figure 1A:
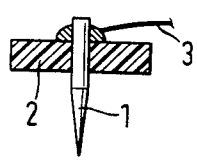
FIG. 1 shows a measuring sensor of a design according to the invention with a single electrode in three embodiments (parts (a) to (c) in a sectional representation, and part (d) in a plan view from below)
Figure 1B:
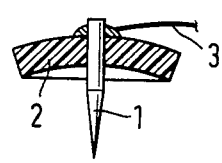
Figure 1C:
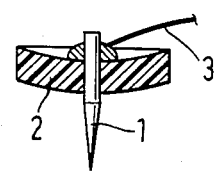
Figure 1D:
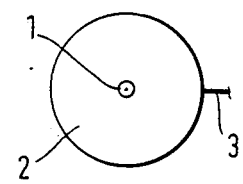
Figure 2A:
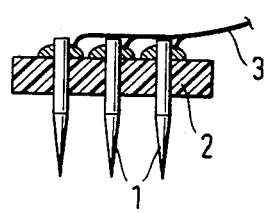
FIG. 2 shows a measuring sensor with an electrode having multiple needle points in two embodiments (parts (a) and (b) in a sectional representation, and part (c) in a plan view from below)
Figure 2B:
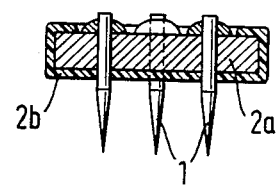
Figure 2C:
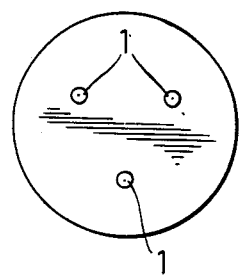

As illustrated, the measuring sensor according to FIG. 2 has an electrode with several needle points 1 which either, part Figure (a), are embedded insulated in a plastic mounting 2 and connected electrically conductively to the conductor 3, or (part Figure (b)) are retained in a conductive mounting 2a which connects the points conductively, but is itself covered with an insulation layer 2b.

Figure 3:
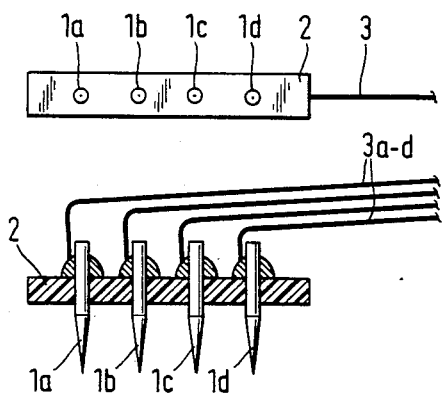
FIG. 3 shows a measuring sensor with a multiple electrode in the form of a row.

In the measuring sensor according to FIG. 3 with a multiple electrode in the form of a row, each individual electrode is shown supported, for example, in a way corresponding to FIG. 1 or FIG. 2.

Figure 4:
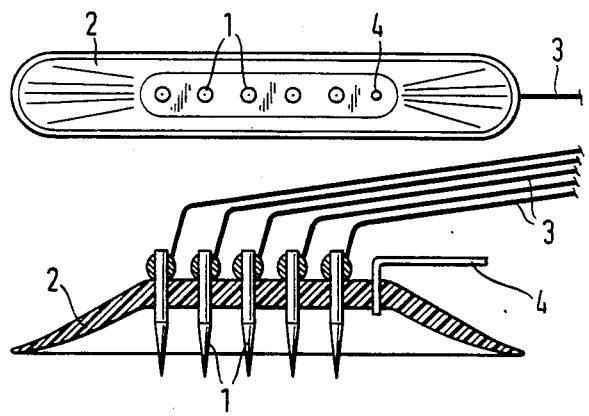
FIG. 4 shows a measuring sensor with a row of single electrodes combined with a suction device.

In the measuring sensor according to FIG. 4, a row of individual electrodes is inserted into a mounted 2 which is designed as a suction cup and which can be connected to a vacuum line via a leading-in tube 4.

Figure 5:
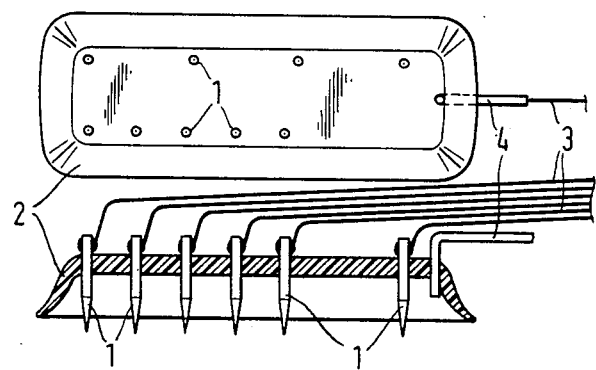
FIG. 5 shows a measuring sensor with an array of individual electrodes, for example combined with a function device.

The measuring sensor according to FIG. 5 with an array of individual electrodes is again combined with a suction device.

Figure 6:
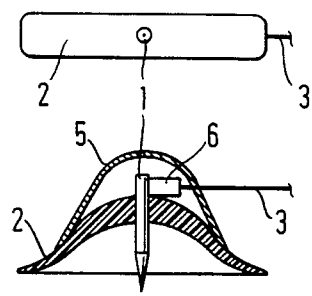
FIG. 6 shows a measuring sensor with an electrode in a preformed mounting.

FIG. 6 then shows a measuring sensor with features according to the invention, in which the single electrode 1 is inserted into a mounting 2 designed as a preformed plastic carrier of bell-shaped cross-section and is covered by a metal screen 5. The measuring electrode 1 is connected directly to the miniaturized preamplifier or transducer 6 above the mounting 2 and within the screen 5. Of course, preamplifier or transducer 6 may be employed in any of the abovedescribed measuring sensor embodiments.

The principle of the invention has already been tested successfully in practice for single electrodes, double electrodes and for multi-electrodes arranged in a row or in a two-dimensional array (for example similar to a matrix) at different distances from one another depending on the intended use. Where multiple electrodes are concerned, preformed or flexible mounting materials have proved particularly advantageous.

Figure 7:
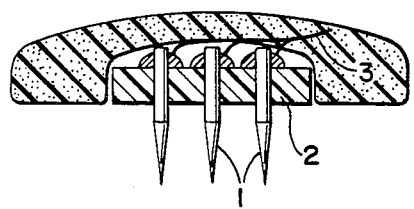
FIG. 7 shows a resilient foam piece for fastening the measuring sensor to a skin surface.

The fastening of the measuring-sensor arrangement to the skin surface has been tested by the methods of (a) adhesion, a resilient foam-rubber material providing the necessary contact pressure (see FIG. 7), (b) attachment by means of bands which are looped resiliently round the appropriate body parts and which press the electrodes down, and (c) suction on the skin surface in conjunction with a suction-electrode arrangement made of flexible rubber material.

The last-mentiond method (c) in particular has proved particularly practicable and convenient, thus providing a substantial time saving in the clinic.

While only certain embodiments of the invention have been specifically described herein, it will be apparent that many modifications and variations to the invention are possible in light of the above teachings without departing from the spirit and scope of the invention. It is therefore to be understood that, within the scope of the appended claims, the invention may be practiced otherwise than as specifically described.

What is claimed is:

1. A measuring sensor for the noninvasive detection of electro-physiological quantities, comprising:
   at least one electrode with a fine needle-like point for local conduction, said electrode being covered with an insulation layer except at an outermost tip of the needle-like point, and said needle-tip point being produced from electrode material and being covered with a salt layer;
   an insulating plastic sheet-like mounting in which the at least one electrode is mounted with the needle-like point extending therefrom, the outermost tip of the needle-like point being positioned at a predetermined distance from the mounting so as to limit penetration of the at least one electrode to uppermost horny cell layers of a patient's skin; and
   a miniaturized active preamplifier connected directly to the at least one electrode;
   wherein the at least one electrode is fastenable to a skin surface of a patient by means of the sheet-like mounting such that, during measurement, penetration of the at least one electrode into the skin surface is limited to the predetermined distance so that only the uppermost horny cell layers of the skin are pierced.

2. A measuring sensor according to claim 1, wherein the at least one electrode has several needle-points.

3. A measuring sensor according to claim 1, wherein several electrodes are arranged at a distance from one another in the sheet-like mounting in a row or in a two-dimensional array and are connected by means of the sheet-like mounting.

4. A measuring sensor according to claim 3, wherein the electrodes are connected flexibly to one another by means of the sheet-like mounting.

5. A measuring sensor according to claim 1, wherein the sheet-like mounting is designed in the form of a suction cup and can be connected to a vacuum line.

6. A measuring sensor according to claim 1, further comprising a resilient foam piece surrounding the sheet-like mounting for fastening the measuring sensor to the skin surface.

7. A measuring sensor according to claim 1, wherein said salt layer comprises AgCl.

8. A measuring sensor for the non-invasive detection of electro-physiological quantities, comprising:
   at least one electrode with a fine needle-like point for local conduction, said electrode being covered with an insulation layer except at an outermost tip of the needle-like point, and said needle-like point being produced from electrode material and being covered with a salt layer;
   an insulating plastic sheet-like mounting is which the at least one electrode is mounted with the needle-like point extending therefrom, the outermost tip of the needle-like point being positioned at a predetermined distance from the mounting so as to limit penetration of the at least one electrode to uppermost horny cell layers of a patient's skin; and
   a miniaturized active transducer connected directly to the at least one electrode;
   wherein the at least one electrode is fastenable to a skin surface of a patient by means of the sheet-like mounting such that, during measurement, penetration of the at least one electrode into the skin surface is limited to the predetermined distance so that only the uppermost horny cell layers of the skin are pierced.

* * * * *